United States Patent [19]

Winslow, Jr. et al.

[11] 3,980,542
[45] Sept. 14, 1976

[54] FLUSH MOUNTED PROBE FOR CORROSION TESTING

[75] Inventors: Joseph D. Winslow, Jr.; Weldon D. Mayse, both of Houston, Tex.

[73] Assignee: Petrolite Corporation

[22] Filed: July 14, 1975

[21] Appl. No.: 595,989

[52] U.S. Cl. ............................ 204/195 C; 204/225; 204/286; 204/297 R; 324/65 CR; 73/86
[51] Int. Cl.² ................. G01N 27/46; G01N 27/30
[58] Field of Search ............. 204/1 C, 195 C, 280, 204/286, 225; 324/29, 65 CR, 71 R; 23/253 C; 73/86

[56] References Cited
UNITED STATES PATENTS

| | | | |
|---|---|---|---|
| 3,166,485 | 1/1965 | Lloyd | 204/1 C |
| 3,558,462 | 1/1971 | Wilson | 204/195 C |
| 3,846,795 | 11/1974 | Jones | 340/421 |
| 3,910,830 | 10/1975 | Mayse | 204/195 C |

Primary Examiner—John H. Mack
Assistant Examiner—Aaron Weisstuch
Attorney, Agent, or Firm—Emil J. Bednar

[57] ABSTRACT

A flush mounted probe for corrosion testing by assembling into a nipple secured to a pipeline. The nipple is of conventional design such as employed in hot tapping installations. The probe is arranged upon assembly within the nipple to place a plurality of planar-surfaced metallic electrodes in substantially parallel alignment with the inner surface of the sidewall of the pipeline. The probe is arranged by its construction for installation and removal in the same manner as blind plugs and other assessories using the hot tapping equipment. No special tools or parts are required to install and remove the present probe, even under extremely elevated pressure conditions in a pipeline.

13 Claims, 4 Drawing Figures

U.S. Patent  Sept. 14, 1976  3,980,542
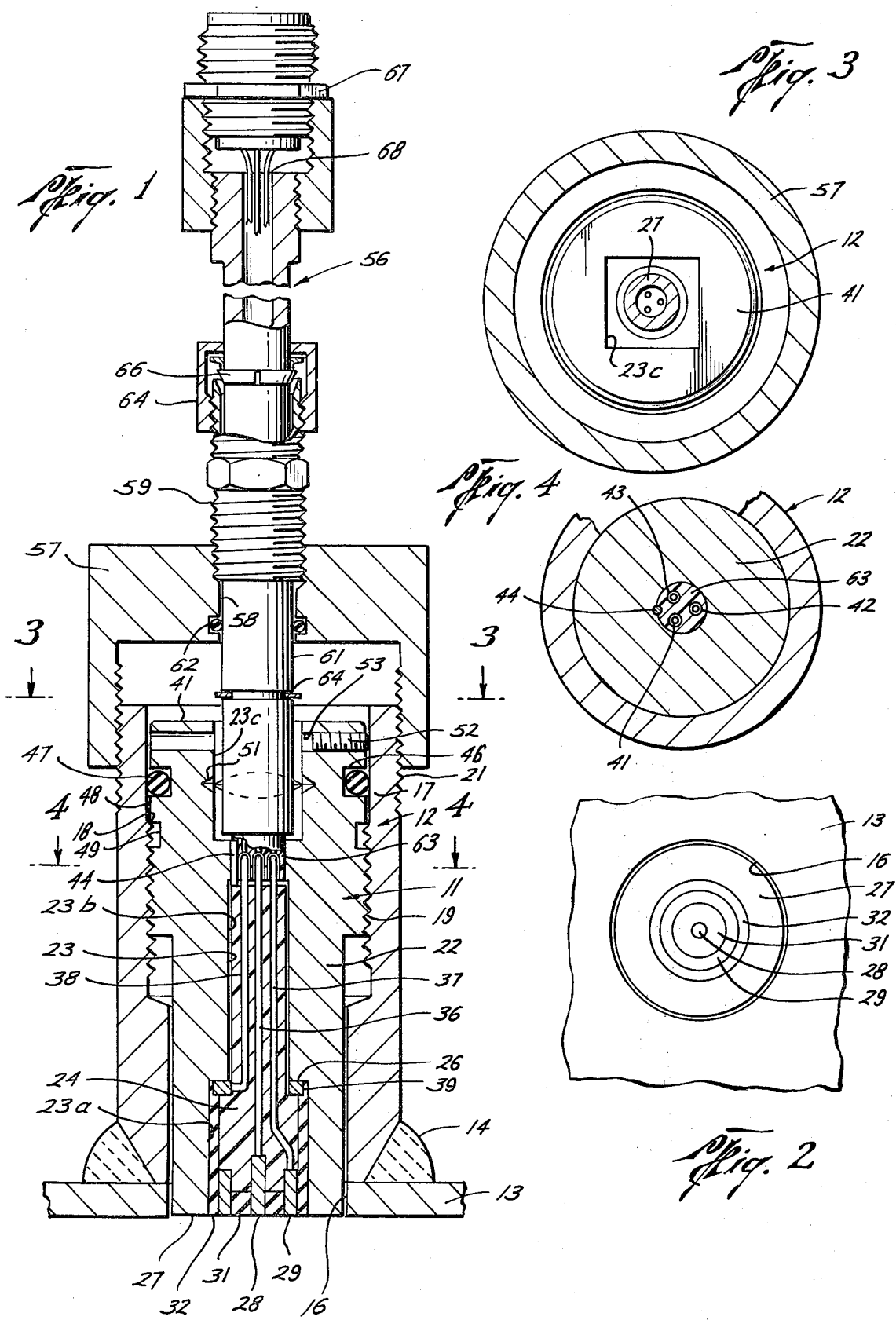

FLUSH MOUNTED PROBE FOR CORROSION TESTING

BACKGROUND OF THE INVENTION

1. Field of the Invention

This invention relates to measuring and testing corrosion processes, and relates particularly to the instruments and electrochemical techniques used in the study of corrosion processes.

2. Description of the Prior Art

The determination of corrosion attack within pipelines carrying corrosive liquids or gases at high pressures is becoming increasingly important for operating safety and monitoring the selective addition of corrosion inhibitors. The transmission of combustible fluids from source to market is provided by pipelines which may vary in dimension from a few inches in diameter to as large as several feet in diameter. Many of these pipelines operate at elevated pressures as high as 1400 psi. There are approximately a million miles of pipelines within the United States which could be damaged from undetected corrosion. In many of these pipelines, a sufficient amount of a liquid aqueous phase is present that a polarization-type corrosion detecting probe and instrument may be employed. It has been found that even in high-pressure gas lines, a very thin film of water coats the interior surface of the pipeline. The placement of the corrosion sensing electrodes of the corrosion prove within such liquid film is essential for proper corrosion measurements.

A probe assembly has been developed for the polarization determination of corrosion effects within a pipeline. This new probe assembly provides for precise placement of planar surfaced electrodes in parallel alignment with the inner surface of the pipeline and within the thin liquid film carried therein. This unique flush-mounted probe assembly is described in U.S. Pat. No. 3,910,830. In a preferred embodiment of the probe assembly, a novel probe is removably mounted within an internally shouldered nipple welded to the pipeline by "hot tapping" techniques. The probe has a cylindrical body with an annular seal adjacent to a sensing head which carries the flat-surfaced metal electrodes. An adjustment nut threadily mounts on a reduced diameter rear portion of the body and engages the shoulder on the nipple to precisely position the electrodes in parallel alignment with the inner wall surface of the pipeline. The nut is adjusted and locked on the body after measurements of the relative longitudinal dimensions from the shoulder to the interior wall surface of the pipeline. This unique flush-mounted probe assembly has found acceptance in corrosion measurements of pipeline but requires careful hot-tapping techniques for installation and removal.

Installations of flush-mounted probe assemblies are usually made in the field by non-technical personnel who are accustomed to installing valves, coupon holders, blind plugs and like fittings with conventional hot-tapping machines. The flush-mounted probe of the present invention has appearance, construction, and function to be completely compatible with the normal nipples and fittings employed in hot-tapping operations in pipelines. Additionally, the present flush-mounted probe does not require technical personnel, such as corrosion engineers, for proper installations and usuage.

It is preferred for rapid and accurate results with this novel flush mounted probe to measure the corrosion occuring within a pipeline by employing the electrochemical process and apparatus generically described in U.S. Pat. No. 3,406,101. In this technique, there is employed a corrosion ratemeter which connects with a probe having three metal electrodes adapted to be exposed to a corrosive liquid. The instrumentation includes an adjustable current source, an ammeter, and a high impedance volt meter as the primary components. The adjustable current source applies a small electric current between a "test" electrode and an auxiliary "electrode." At the same time, the volt-meter monitors the induced polarization potential between the test electrode and a "reference" electrode. The current flow slightly polarizes the surface of the test electrode, and as a result, causes a shift in the potential between the test and reference electrodes. The current flow required to produce about 10 millivolts polarization is directly proportional to the corrosion rate of the test electrode undergoing corrosion.

In many pipelines the effects of corrosion are very long term and should be monitored on a continuous basis over a selected period of time. One corrosion ratemeter for industrial monitoring of corrosion effects for extended periods of time is shown in U.S. Pat. No. 3,717,566. This corrosion ratemeter is automatic in operation between nulling and recording with a permanent chart record of highly accurate measurements of corrosion over extended periods of time. If desired, other corrosion ratemeters of similar manufacture for making corrosion measurements may be employed to advantage.

It is especially advantageous to employ these automatic recording corrosion ratemeters with the novel probe assembly of this invention for monitoring directly the corrosion occurring in pipelines. The flush mounted probe of the present invention provides simple, easy, and full-proof introduction of sensing electrodes into the pipeline to be monitored in such a manner that the flat-surfaced electrodes are precisely aligned with the inner sidewall surface of the pipeline. Normal operation of the pipeline is not disturbed. The placement of the flush mounted probe is completely conventional by hot-tapping techniques within the pipeline. Other results provided by the present flush mounted probe will be appreciated from the following discussion.

SUMMARY OF THE INVENTION

In accordance with this invention, a flush mounted probe is provided for performing corrosion tests by assembling into a nipple secured to a pipeline. An opening is provided through the sidewall of the piepline in axial alignment with the nipple. The nipple has a first portion with a smooth-walled inner surface, a second portion forming an abutment means, and a third-portion carrying interior threads. The flush mounted probe has a cylindrical metallic body with a terminal planar surface including an insulating medium and electrodes at one end thereof. The planar surface is normal to the longitudinal axis of the body. A plurality of metallic electrodes are integrally carried on the body in electrical isolation relative to one another. The electrodes reside in a spaced apart relationship with the intervening spaces filled by the insulating medium. Exterior threads on the body engage the threads on the third portion of the nipple for mounting the probe within the nipple. Sealing means encircle the body to cooperate with the smooth-walled inner surfaced of the first portion of the nipple for forming a fluid-tight seal between the body and nipple. Stop means are carried on the body to engage the abutment means on the nipple so that the planar surface on the body is positioned adjacent the interior sidewall surface of the pipeline. The body has a drive member means formed at a second end which is adapted to be engaged by a tool for transmitting rotary force to the body. The body also carries latching means for selectively securing the tool to the drive member means. Terminals are carried by the body within an axial opening extending from the terminals to the second end of the body. The terminals are interconnected by electrically conductive means to the electrodes. Indexing means are provided on the body adjacent the terminals and have a predetermined orientation with respect to the terminals.

DESCRIPTION OF THE DRAWINGS

FIG. 1 is an elevational view in section showing the flush mounted probe of the present invention mounted within an nipple secured to the pipeline and carrying an external circuit connector for connection to a suitable corrosion ratemeter;

FIG. 2 shows the electrode carrying end of a flush-mounted probe of FIG. 1 as viewed from the interior of the pipeline;

FIG. 3 is a cross-section taken along line 3—3 of FIG. 1; and FIG. 4 is a cross-section taken along line 4—4 of the Flush Mounted Probe of FIG. 1.

DESCRIPTION OF SPECIFIC EMBODIMENTS

Referring now to FIG. 1, there is shown a flush mounted probe 11 of the present invention secured within a nipple 12 upon a pipeline conduit 13. The nipple 12 is secured to the conduit 13 by a weld 14. The inner sidewall of the conduit 13 is provided with an opening 16 which is in alignment with the nipple 12. The nipple 12 can be of conventional construction such as commonly employed for the mounting of various devices to a pipeline by hot-tapping techniques. For example, the nipple 12 may be a 2 inches diameter "T-O-R" nipple available to the pipeline industry from T. D. Williamson, Inc. of Tulsa, Oklahoma.

The nipple 12 has a first portion with a smooth-walled inner surface 17, a second portion forming an abutment 18 and a third portion carrying interior threads 19. The abutment 18 can be provided by the base cut of the threads 19 at their top most extremity as seen in FIG. 1. The arrangement of the first, second and third portions of the nipple 12 is preferably as shown in the drawings. After the nipple 12 is secured to the pipeline conduit 13, a hot tapping-drilling machine such as T. D. Williamson, Inc. T-101 drilling machine is secured through a tapping valve to the nipple 12 upon external threads 21. The drilling machine, and the tapping valve secured upon the threads 21 are not shown in the drawings but such an arrangement is conventional in the art. Then the drilling machine provides the opening 16 within the sidewall of the pipeline conduit 13. The drilling machine is then retracted and the tapping valve closed for sealing the nipple 12 to the atmosphere. The bit is removed from the drilling machine and the probe 11 attached. Then, the machine is operated to move the probe 11 into threaded engagement with the nipple 12. The probe 11 is rotated until seating itself upon the abutment 18 of the nipple 12. At this time the machine is retracted and the tapping valve is closed and removed. The probe 11 is secured and sealed fluid-tight within the nipple 12 so that fluid cannot leak from the pipeline 13 to the surrounding atmosphere. It will be apparent that the mounting of the probe 11 within the nipple 12 is exactly the same as the placement of a blind plug such as used to permit recovery of tapping valves.

The probe 11 has a unique construction for installation and and removal from the nipple 12 by conventional hot-tapping machines available to the pipeline industry. In a preferred embodiment, the probe 11 has a cylindrical metal body 22 with an axial passageway 23 of circular cross-section. The passageway 23 can have a uniform diameter throughout the body 22 but preferably, the passageway 23 has several different diameter parts 23a, 23b, and 23c. A rigid insulator 24 is carried in the enlarged diameter part 23a formed in passageway 23. As a result, the insulator 24 is seated against a shoulder 26 formed within the body 22 and held against displacement by fluid pressure in the pipeline conduit 13. The rigid insulator 24 integrally carries one or more electrodes in a laterally spaced apart relationship at a first end 27 of the body 22 which is formed into a terminal planar surface. Although three electrodes can be carried within the insulator 24, preferably, the insulator 24 carries only electrodes 28 and 29. If desired, a third electrode is provided by the flat surface on the annular portion of the body 22 at its first end 27. The electrodes have flat surfaces exposed to corrodent and aligned with the inner surface of the pipeline conduit 13. With this arrangement in the probe 11, the electrode 28 serves as the reference, the electrode 29 serves as the test, and the body 22 serves as the auxiliary electrode for corrosion measurements. The body 22 not only provides an electrode but also protects the electrodes 28 and 29 against physical injury from indiscreet handling by field personnel.

The electrodes of probe 11 may be of any suitable construction but are preferably formed with circular configurations in the planar surface as can be seen by momentary reference to FIG. 2. The electrode 28 is a metal rod which is spaced apart from an annular metal electrode 29 by an intervening insulating material annular segment 31. Another annular segment 32 of the insulating material separates the electrode 29 from the annular enclosing first end 27 of the body 22 that provides the third electrode.

Returning to FIG. 1, the insulating medium of segment 32 also extends into and fills in fluid tightness the annulus between the insulator 24 and the body 22 throughout the part 23a of the passageway 23. Thus, the insulating medium not only fills completely the intervening spaces between the electrodes but provides a fluid seal between the rigid insulator 24 and the body 22. The insulating material is contained downstream by an imperforate wall thereby producing a pressure actuated seal. Thus, fluid pressure within the pipeline conduit 13 acts directly upon the exposed surfaces of the insulating medium to insure adequate sealing pressure between the insulating medium, the body 22, and the rigid insulator 24. Various resilient materials can provide the insulating medium but it is preferred to use a moldable elastomer 32. A water-wetted synthetic rubber, such as Viton or Buna N has been used with good results. The insulating medium fills void free the spaces between the electrodes, insulator 24 and the body 22 of the probe 11.

The rigid insulator 24 is fabricated from a dielectric material which preferably is a glass-filled epoxy that can be cast in molds to the desired configuration. The insulator 24 can be produced in the following manner. Electrodes 28 and 29 are connected to electrical conductors 36 and 37 respectively. An addition electrical conductor 38 carrying a ring 39 is placed into a mold with the other electrodes and conductors properly oriented. The mold is filled with the castable glass-filled epoxy. The glass-filled epoxy hardens to form the insulator 24.

The electrical conductors 36, 37, and 38 extend through the insulator 24 into the reduced second diameter part 23b of the passageway 23 and form terminal pins 41, 42, and 43, respectively. Preferably, these terminal pins project a uniform distance from the insulator 24. Referring momentarily to FIG. 4, these terminal pins can have any orientation. Preferably, the terminals are arranged in an equal-spaced triangular arrangement within the passageway 23.

An indexing structure is carried in the passageway 23 which has a predetermined spacial orientation with respect to the terminal pins. For example, an indexing pin 44 is molded into the insulator 24 in the same manner as the electrical conductors. For best results, the indexing pin 44 projects from the insulator a short distance beyond the terminal pins 41, 42 and 43. In this manner, the indexing pin 44 guides a female electrical conductor into proper radial orientation with subsequent longitudinal positioning about the terminal pins 41, 42 and 43 for electrical innerconnection.

The body 22 carries a sealing structure providing a fluid-tight joint between the probe 11 and the nipple 12. Any suitable seal arrangement may be employed. However it has been found a pressure actuated seal produces the most desired sealing function. This function can be provided by an annular goove 46 about the body 22 opposite the smooth-walled surface 17 of the nipple 12. An O Ring 47 is carried within the recess 46 and engages the smooth-walled inner surface 17 of the nipple 12 to form a fluid-tight seal. Other types of sealing mechanisms could be employed, if desired. However, placing the seal at the second end of the body 22 protects it against inadvertent injury by the threads 19 and other sharp edged projections.

The probe 11 at its first end 27, electrodes 28 and 29, and the intervening segments 31 and 32 of insulating material form a common terminal planar surface which is aligned transversely to the longitudinal axis of the body 22. The probe 11 is constructed so that this terminal planar surface will reside in substantial alignment with the inner surface of the pipeline conduit 13 with the probe mounted in the nipple 12.

In order to insure that the probe 11 will thread only to the desired longitudinal entry within the nipple 12, but not any further, the body 22 carries a stop member 48 to engage the abutment 18 on the nipple 12. The stop member 48 can be provided by a projection on the body 12 which overlaps and seats upon the uppermost surfaces of the threads 19 on the nipple 12. Clearance for the cutting of the threads 19 is provided by a recess 49 within the body 22 immediately below the stop member 48. Other arrangements for limiting the longitudinal entry of the probe 11 into the nipple 12 may be employed, if desired.

The probe 11 will usually be threadedly secured within the nipple 12 through the use of a hot-tapping machine when there is fluid pressure in the pipeline conduit 13. Therefore, the body 22 has a drive member which can be engaged by such a machine to impart the desired rotary force for threading and unthreading the probe 11 relative to the nipple 12. Various arrangements can produce the needed drive connection between the probe 11 and a tool (boring bar) in the machine for imparting rotary motion to various pieces of equipment such as blind plugs employed in hot-tapping techniques. In the present embodiment, the drive member is provided in the third part 23c of the passageway 23 by a cross sectional opening larger than the second part 23-b. Preferably, the third part 23c of the passageway is formed at least in part with a polygonal cross-section which is adapted in size and shape to engage the tool required for transmitting rotary force to the probe 11. Referring briefly to FIG. 3, the opening 23c can have a "square" cross-section, which configuration is conventional for the tool of a hot-tapping machine providing rotary motion for seating blind plugs and the like. If desired, other structural arrangements for providing the drive member upon the probe 11 may be used.

It is also advantageous to provide the body 22 with a latching mechanism for selectively securing the probe 11 to the tool providing the rotary motion. Preferably, the third part 23c of the passageway carries a detent, such as groove 51 for selectively securing the tool to the probe 11. For this purpose, the tool may carry a spring loaded ball which is forced outwardly into engagement with a V-shaped groove 51 formed into the interior side surface of the body 22 surrounding the opening 23-c. Thus, the tool may be snapped into the opening 23-c for suspending the flush-mounted probe while the probe is threaded within the nipple 12. After the probe 11 is in the desired position within the nipple, the tool is unsnapped and the hot-tapping machine is removed.

The probe 11 may be locked in place so as not to be inadvertently displaced from nipple 12. For this purpose, the body 22 can be provided with a locking mechanism so that the probe 11 can not be unthreaded from the nipple 12. Although various locking mechanisms are available, it is preferred to use a set screw 52 which is threaded into an opening 53 extending to the exterior of the body 22. The screw 52 engages the nipple 12 in firm metal-to-metal contact to insure that the probe 11 will not be inadvertently unthreaded from the nipple 12 while the pipeline conduit 13 carries high-pressure fluid. The set screw 52 has an Allen-head so that it may be engaged by an Allen wrench through the opening 23c in an expeditious manner. Now, the probe 11 is ready for use in making corrosion tests by connection of suitable instrumentation to the terminal pins 41, 42 and 43 that are connected to the several electrodes. If immediate measurements are not desired, or for other reasons, a solid pipe cap may be threaded over the nipple 12.

With the probe 11 mounted in the nipple 12, any suitable electrical connection can be made to an external instrument for monitoring the corrosion phenomenon occurring within the pipeline conduit 13. The arrangement shown in FIG. 1 is especially useful with the probe 11 for long term measurements. An external electrical connector 56 is recommended for use with the probe 11 since the probe 11 is protected against rain, snow and other natural injury, and also provides safety features for the instrument operators. in particular, the connector 56 mounts to the nipple 12 by the use of a threaded pipe cap 57 received upon the threads 21. The cap 57 carries an opening 58 which is partially threaded to receive a tubing fitting 59. A metal tube 61 extends through the cap 57 and fitting 59 and is sealed in fluid tightness to the cap 57 by an O ring 62. The inner end of the tube 61 carries a female plug 63 which is adapted to provide electrical connection with the terminal pins of the probe 11. It is desirable to limit the outward movement of the tube 61 from the cap 57 since a pressure build-up through seal-failure about the probe 11 could propell the tube outwardly with injurious force. Any suitable mechanism may be employed for such movement limiting but a half-moon ring 64 placed within a recess in the exterior surface of the tube 61 will engage the cap 57 and limit outward movement.

The tube 61 is moved inwardly so that the plug 63 aligns an indexing pin 44 for ready connection with the terminal pins of the probe 11. Now, the nut 64 is tightened so that the ferrule assembly 66 engages the tube 61 and the fitting 69 in a fluid-tight, mechanical-rigid engagement. Thus, the connector 56 provides a mechanical back-up safety feature should the fluid seal on the probe 11 fail while an operator is making corrosion measurements. With the described arrangement, neither direct fluid-leakage nor fluid-induced movement impressed upon the connector 56 can produce injury to the operator. The upper extremity of the tube 61 carries a suitable electrical fitting 67 for ready connection to the desired instrumentation. A plurality of electrical conductors 68 connect the fitting 67 to the female plug 63 so that proper electrical connections are made between the instrumentation and the probe 11.

It is envisioned that the probe 11 may be constructed with other placements of the sealing, abutment, and the threaded portions where required by other configurations of the nipple 12. These changes and other variations can be readily using known devices employed in the hot-tapping installation of equipment upon pipelines.

From the foregoing, it will be apparent that there has been provided a flush-mounted probe for performing corrosion tests by assembling into a nipple secured upon a pipeline. In particular, this probe provides for the electro-chemical monitoring corrosion phenomena in a pipeline conduit and yet for all practical purposes is placed into position as other pipeline devices such as blind pipe plugs. Various changes and modifications may be made to the structure of the present flush-mounted probe without departing from the spirit of the invention. It is intended that the present description be taken in illustration of the invention, and the appended claims define the scope thereof.

What is claimed is:

1. A flush mounted probe for performing corrosion tests by assembly into a nipple secured to a pipeline which has an opening through its sidewall in axial alignment with the nipple, and the nipple has a first portion with a smooth-walled inner surface, a second portion forming an abutment means, and a third portion carrying interior threads comprising:
   a. a cylindrical metallic body with a terminal planar surface formed by an insulating medium at a first end thereof,
   b. a plurality of metallic electrodes disposed within said body and in electrical isolation relative to one another, said electrodes residing in a spaced apart relationship with the intervening spaces filled by said insulating medium and said electrodes having flat surfaces coinciding with said planar surface;
   c. exterior threads on said body between said first end and a second end thereof for engaging the threads on the third portion of said nipple for mounting the probe in the nipple;
   d. sealing means carried circumferentially about said body between said exterior threads and said second end thereof to cooperate with the straight-walled inner surface of the first portion on the nipple for forming a fluid tight seal between said body and the nipple;
   e. stop means carried on said body to engage the abutment means on the nipple whereby said planar surface of said body is positioned adjacent the interior sidewall surface of the pipeline;
   f. drive member means formed on said body at said second end and adapted to be engaged by a tool for transmitting rotary force to said body wherein said drive member means is provided by a coaxial opening extending into said second end of said body and said opening having a polygonal cross section;
   g. latching means carried by said body in said coaxial opening for selectively securing the tool to said drive member means;
   h. terminals carried by said body within an axial opening extending from said terminals to said coaxial opening in the second end of said body and said terminals interconnected by electrically conductive means to said electrodes, and
   i. indexing means on said body adjacent said terminals and having a predetermined orientation with respect to said terminals.

2. The flush mounted probe of claim 1 wherein said body adjacent the second end thereof carries a locking means for securing the probe within the nipple against inadvertent displacement.

3. The flush mounted probe of claim 1 wherein said sealing means is provided by an annular recess formed within said body adjacent the second end thereof and an O-ring disposed in said recess.

4. The flush mounted probe of claim 1 wherein said latching means is provided by detent means carried on said body within said drive member means.

5. A flush mounted probe for performing corrosion tests by assembly into a nipple secured to a pipeline which has an opening through its sidewall in axial alignment with the nipple, and the nipple has a first portion with a smooth-walled inner surface, a second portion forming an abutment means, and a third portion carrying interior threads comprising:
   a. a cylindrical metallic body with an axial passageway therethrough;
   b. a rigid insulator carried in a first part of said axial passageway and mounting one or more metallic electrodes in a lateral spaced apart relationship at a first end of said body;
   c. each of said metallic electrodes projecting longitudinally beyond said rigid insulator to the first end of said body and being electrically isolated from one another by a fluid-impervious insulating medium filling substantially completely the spaces between said electrodes and extending to the longitudinal extremity each of said electrode and body each of said metallic electrodes and said insulating medium having a common terminal planar surface at said first end of said body;

d. sealing means carried circumferentially about said body adjacent a second end thereof to cooperate with the smooth-walled inner surface of the nipple thereby forming a fluid-tight seal therebetween;
e. stop means carried on said body to engage the abutment means on the nipple whereby said terminal planar surface including said electrodes, said insulating medium and said body is positioned adjacent the interior wall surface of the pipeline;
f. drive member means formed on said body at the second end thereof and adapted to be engaged by a tool for transmitting rotary force to said body, wherein said drive member means is provided by a coaxial opening adjacent said second end of said body having a polygonal cross section;
g. latching means carried by said body for selectively securing the tool to said drive socket means;
h. exterior threads on said body between said sealing means and the first end thereof for engaging the threads on the third portion of the nipple to secure said probe therein;
i. terminals carried in said axial passageway by said rigid insulator adjacent the coaxial opening at the second end of said body, said terminals and each of said electrodes and said body being interconnected by electrically conductive means within said rigid insulator; and
j. indexing means integrally carried by said body and having a predetermined orientation with respect to said terminals.

6. The flush mounted probe of claim 5 wherein said body adjacent the second end thereof carries a locking means for securing the probe within the nipple against inadvertent displacement.

7. The flush mounted probe of claim 5 wherein said sealing means is provided by an annular recess formed within said body adjacent the second end thereof and an O-ring disposed in said recess.

8. The flush mounted probe of claim 5 wherein said latching means is provided by detent means carried on said body within said drive member means.

9. A flush mounted probe for performing corrosion tests by assembly into a nipple secured to a pipeline which has an opening therethrough in its sidewall in axial alignment with the nipple, and the nipple has a first portion with a smooth-walled inner surface, a second portion forming an abutment means, and a third portion carrying interior threads comprising:
a. a cylindrical metallic body with an axial circular-cross sectioned passageway therethrough;
b. a rigid insulator carried in an enlarged diameter first part of said passageway and seated against an interior shoulder in said passageway in said body, said rigid insulator mounting one or more metallic electrodes in a lateral spaced apart relationship at a first end of said body;
c. each of said metallic electrodes projecting longitudinally beyond said rigid insulator to the first end of said body and said electrodes being electrically isolated from one another and said body by a fluid-impervious insulating medium filling substantially the spaces between said electrodes and body and extending to the longitudinal extremity of each of said electrodes and body, each of said electrodes and said insulating medium having a common terminal planar surface at said first end of said body;
d. sealing means carried circumferentially about said body at a second end thereof to cooperate with the smooth-walled inner surface of the nipple thereby forming a fluid-tight seal therebetween;
e. stop means carried on said body to engage the abutment means on the nipple whereby said terminal planar surface of said body is positioned adjacent the interior wall of the pipeline;
f. exterior threads on said body between said sealing means and the first end thereof adapted to engage the threads on the third portion of the nipple to secure said probe therein;
g. said rigid insulator extending toward the second end of said body to a reduced diameter part of said passageway, terminal pins extending longitudinally toward said second end of said body and mounted at the interior extremity of said rigid insulator, and said terminal pins interconnected by electrically conductive means to each of said electrodes and body;
h. drive member means formed on said body at the second end thereof and including a third part of said passageway having an opening larger than the reduced diameter part containing said rigid insulator at its interior extremity, and said third part of said passageway having at least in part a polygonal cross-section adapted to be engaged by a tool for transmitting rotary force to said body;
i. latching means carried by said body for selectively securing the tool to said drive member means and including detent means within said third part of said passageway; and
j. indexing means carried by said body in said passageway adjacent said terminal pins and having a predetermined orientation with respect to said terminal pins.

10. The flush mounted probe of claim 9 wherein said indexing means is a terminal-like pin carried in said rigid insulator and extending longitudinally a greater distance from said rigid insulator than said terminal pins.

11. The flush mounted probe of claim 9 wherein locking means are carried on said body adjacent its second end for securing said probe within the nipple against inadvertent displacement.

12. The flush mounted probe of claim 11 wherein said locking means are a set screw threadedly mounted in said body for lateral movement from said third part of said passageway to the exterior of said body.

13. The flush mounted probe of claim 9 wherein said exterior threads reside intermediate the length of said body and said sealing means are carried about said body between the second end thereof and said exterior threads.

* * * * *

UNITED STATES PATENT AND TRADEMARK OFFICE
CERTIFICATE OF CORRECTION

PATENT NO. : 3,980,542
DATED : September 14, 1976
INVENTOR(S) : Joseph D. Winslow Jr. et al It is certified that error appears in the above—identified patent and that said Letters Patent are hereby corrected as shown below:

Column 5, line 29, for "conductor", read ---connector---;

Column 6, line 67, for "operators. in", read ---operators. In---;

Column 7, line 5, for "0 ring", read ---"O" ring---;

Column 8, line 19 (Claim 1), after "body", insert a comma ---(,)---; and

Signed and Sealed this

Fourth Day of January 1977

[SEAL]

Attest:

RUTH C. MASON
Attesting Officer

C. MARSHALL DANN
Commissioner of Patents and Trademarks

UNITED STATES PATENT AND TRADEMARK OFFICE
CERTIFICATE OF CORRECTION

PATENT NO. : 3,980,542
DATED : September 14, 1976
INVENTOR(S) : Joseph D. Winslow, Jr. and Weldon D. Mayse It is certified that error appears in the above-identified patent and that said Letters Patent are hereby corrected as shown below:

Column 1, line 31, for "prove", change to read --- probe ---

Column 8, line 65, after "body", insert a comma (,)

*Signed and Sealed this*

Fifteenth Day of February 1977

[SEAL]

Attest:

RUTH C. MASON
*Attesting Officer*

C. MARSHALL DANN
*Commissioner of Patents and Trademarks*